(12) United States Patent
Norris

(10) Patent No.: US 6,505,060 B1
(45) Date of Patent: Jan. 7, 2003

(54) METHOD AND APPARATUS FOR DETERMINING PULSE OXIMETRY DIFFERENTIAL VALUES

(75) Inventor: Mark A. Norris, Boulder, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 8 days.

(21) Appl. No.: 09/675,707

(22) Filed: Sep. 29, 2000

(51) Int. Cl.$^7$ ................................................ A61B 5/00
(52) U.S. Cl. ...................................... 600/323; 600/336
(58) Field of Search ................................ 600/309–310, 600/322–324, 330, 336

(56) References Cited

U.S. PATENT DOCUMENTS

| | | | |
|---|---|---|---|
| 5,069,214 A | * 12/1991 | Samaras et al. | 600/323 |
| 5,297,548 A | * 3/1994 | Pologe | 600/310 |
| 5,351,685 A | * 10/1994 | Potratz | 600/330 |
| 5,588,427 A | 12/1996 | Tien | |
| 5,687,722 A | * 11/1997 | Tien et al. | 600/323 |
| 5,766,127 A | 6/1998 | Pologe et al. | 600/310 |
| 5,841,523 A | * 11/1998 | Degen et al. | 356/72 |
| 5,853,364 A | * 12/1998 | Baker, Jr. et al. | 600/300 |
| 5,924,980 A | 7/1999 | Coetzee | 600/300 |
| 5,934,277 A | 8/1999 | Mortz | |
| 6,036,642 A | 3/2000 | Diab et al. | 600/364 |
| 6,083,157 A | * 7/2000 | Noller | 600/310 |

* cited by examiner

Primary Examiner—Eric F. Winakur
Assistant Examiner—Matthew Kremer
(74) Attorney, Agent, or Firm—Marsh Fischmann & Breyfogle LLP

(57) ABSTRACT

Differential values, for use in blood oxygenation calculations, are determined based on multiple sample values for each channel of an oximetry system, each such value constituting a data point. In one implementation, each of these data points is defined by a sample window (220, 222 and 224), where the window includes, for example, 7–10 data points. That is, the data points within window (220, 222 or 224) are used to establish a differential value nominally associated with the data sample about which the window is centered. The differential value is calculated based on a mathematical model such as a weighted linear regression analysis. In this manner, output may be provided on a sample-by-sample basis while mitigating noise sensitivity.

38 Claims, 5 Drawing Sheets

DATA POINT

METHOD AND APPARATUS FOR DETERMINING PULSE OXIMETRY DIFFERENTIAL VALUES

FIELD OF THE INVENTION

The present relates in general to processing detector information in a pulse oximetry system and, in particular, to the determination of differential values for use in blood oxygenation calculations with reduced noise sensitivity.

BACKGROUND OF THE INVENTION

In the field of photoplethysmography, light signals corresponding with two or more different centered wavelengths may be employed to non-invasively determine various blood analyte concentrations. By way of example, blood oxygen saturation ($SpO_2$) levels of a patient's arterial blood are monitored in pulse oximeters by measuring the absorption of oxyhemoglobin and reduced hemoglobin using red and infrared light signals. The measured absorption data allows for the calculation of the relative concentrations of reduced hemoglobin and oxyhemoglobin, and therefore $SpO_2$ levels, since reduced hemoglobin absorbs more light than oxyhemoglobin in the red band and oxyhemoglobin absorbs more light than reduced hemoglobin in the infrared band, and since the absorption relationship of the two analytes in the red and infrared bands is known.

To obtain absorption data, pulse oximeters comprise a probe that is releasably attached to a patient's appendage (e.g., finger, ear lobe or the nasal septum). The probe directs red and infrared light signals to the appendage, or tissue-under-test. The light signals are provided by one or more sources which are typically disposed in the probe. A portion of the light signals is absorbed by the tissue-under-test and the intensity of the light transmitted through or reflected by the tissue-under-test is detected, usually by at least one detector that may also be located in the probe. The intensity of an output signal from the detector(s) is utilized to compute $SPO_2$ levels, most typically via a processor located in a patient monitor interconnected to the probe.

As will be appreciated, pulse oximeters rely on the time-varying absorption of light by a tissue-under-test as it is supplied with pulsating arterial blood. The tissue-under-test may contain a number of non-pulsatile light absorbers, including capillary and venous blood, as well as muscle, connective tissue and bone. Consequently, detector output signals typically contain a large non-pulsatile, or DC, component, and a relatively small pulsatile, or AC, component. It is the small pulsatile, AC component that provides the time-varying absorption information utilized to compute arterial $SpO_2$ levels.

In this regard, the red and infrared signal portions of pulse oximeter detector output signals each comprise corresponding large DC and relatively small AC components. The red and infrared signal portions have an exponential relationship to their respective incident intensities at the detector(s). As such, the argument of the red and infrared signal portions have a linear relationship and such portions can be filtered and processed to obtain a ratio of processed red and infrared signal components (e.g., comprising their corresponding AC and DC components), from which the concentration of oxyhemoglobin and reduced hemoglobin in the arterial blood may be determined. See, e.g., U.S. Pat. No. 5,934,277. By utilizing additional light signals at different corresponding centered wavelengths it is also known that carboxyhemoglobin and methemoglobin concentrations can be determined. See, e.g., U.S. Pat. No. 5,842,979.

As noted, the pulsatile, AC component of a pulse oximeter detector output signal is relatively small compared to the non-pulsatile DC component. Consequently, the accuracy of analyte measurements can be severely impacted by small amounts of noise. One such type of noise relates to effects on the measured absorption data as a result of undesired variations in the path length of light signals as they pass through the tissue-under-test. Such variations are most typically caused by patient movement of the appendage to which a pulse oximetry probe is attached.

A number of different approaches have been utilized to reduce the deleterious effects of patient motion in pulse oximeters. For example, pulse oximeter probes have been developed to enhance the physical interface between the probe and tissue-under-test, including the development of various clamp type probe configurations and secure wrap-type probe configurations. Further, numerous approaches have been developed for addressing motion contaminated data through data processing techniques. While such processing techniques have achieved a degree of success, they often entail extensive signal processing requirements, thereby contributing to increased device complexity and componentry costs.

Other types of noise include electrical and optical phenomena that cause artifact in the pulsatile component of the measured absorption data. For example, effects due to ambient light and interfering electrical signals can provide significant noise components. Many of these noise sources are not easily filtered out of the detector signal and, therefore, are reflected in the measured absorption data. It will be appreciated that such noise in the measured absorption data can significantly affect blood oxygen saturation calculations if not adequately accounted for in signal/data processing.

The case of calculating derivatives of the measured absorption data signal is illustrative. As noted above, pulse oximetry blood oxygenation calculations are generally based on measuring the relative time varying absorption or optical signal attenuation at two or more wavelengths by the tissue-under-test. Specifically, a ratio of corresponding differential values, such as the normalized derivative of attenuation (NdA) for each of two centered wavelengths or channels may be calculated. The time derivative of the attenuation divided by the attenuation provides the NdA. The ratio of the NdAs for the red and infrared wavelengths, as often employed in pulse oximeters, is directly proportional to $SpO_2$.

The NdAs for each wavelength have generally been calculated in two ways. Most commonly, the NdAs have been approximated by measuring a peak to trough amplitude of the pulsatile signal. However, this methodology is sensitive to noise at the data points associated with the peak and trough. Moreover, the response time of such pulse oximeters is limited due to the elongated sampling interval required for NdA calculations. Additionally, this methodology can suffer from reduced accuracy if the delays of the high pass AC filters and low pass DC filters, used to separate the pulsatile and non-pulsatile components of the detector signal in connection with peak and trough identification, are not carefully matched. As noted above, calculation of the NdAs involves dividing the time derivative of the attenuation by the overall attenuation including the DC component. This calculation assumes that the time derivative and DC component are sampled at substantially the same time and, accordingly, any differences in the filter delays can introduce an element of error. Additionally, such filters can take considerable time to stabilize before the oximeter can calculate accurate derivatives.

Another common method of estimating the NdA involves calculating a difference between successive data points of the processed detector signal. This difference is normalized by dividing by an average DC value for the two data points. This methodology avoids many of the disadvantages of peak-to-trough calculations, and generates output for every sample, but the change in signal level is much smaller as between successive samples as compared to peak-to-trough amplitude calculations. As a result, individual measurements are sensitive to noise.

In pulse oximetry systems developed by Datex-Ohmeda, Inc., successive data point calculations are employed but multiple data sets are utilized to determine the NdA ratio used for $SpO_2$ calculations thereby improving accuracy. In particular, absorption related values are calculated for each channel for multiple samples over a measurement period. For each sample time during the measurement period, a ratio of the corresponding absorption related values for the channels, e.g., red and infrared, is calculated, thereby yielding a set of ratios. This may be visualized as a graph plotting a number of points as red absorption related values against infrared absorption related values. Ideally, these points define a line and the slope of the line is proportional to $SpO_2$. The slope of the line may be determined, for example, by a linear regression analysis.

The noted Datex-Ohmeda system thus involves two separate processes. First, differential values are calculated using data points of a single channel. Second, a differential analysis is performed on the set of channel-by-channel ratios or graphical data points to determine a slope value. The latter process may involve a linear regression analysis. The former process has been limited to consideration of successive data points.

SUMMARY OF THE INVENTION

The present invention is directed to processing of measured absorption data to obtain differential values, such as NdAs, with reduced noise sensitivity. The invention allows for provision of output at frequent intervals, such as on a sample-by-sample basis, while mitigating noise sensitivity associated with calculating differentials based solely on successive samples e.g., successive measured absorption data points. In order to facilitate accurate detection of noise such as for motion correction, the present invention further allows for separate storage of and access to pre-processed and post-processed data sets, such that post-processed data can be used in analyte calculation algorithms and preprocessed data can be used for making motion or other noise correction calculations.

In accordance with one aspect of the present invention, differential values are determined using a window including non-successive samples, thereby reducing noise sensitivity associated with the sometimes small differential values of successive samples. As noted above, successive sample calculations have certain advantages over peak-to-trough calculations including the ability to generate output for each sample, but are sensitive to noise due to small differential values. A process in accordance with the present aspect of the invention uses windows including non-successive values by: receiving a series of data samples for a single centered wavelength corresponding to a measurement period; defining a moving sampling window that has a time dimension less than the measurement period; accessing first and second data samples within the sampling window for a given sampling interval, where the first and second data samples are separated by an intervening data sample; using the first and second data samples to calculate a differential value; and using the differential value in determining the parameter value related to blood oxygen saturation. The determination of a differential value as reflected in this process may be applied to each of multiple channels, e.g., a red centered wavelength and infrared centered wavelength, to enable channel ratio based $SpO_2$ calculations. This process advantageously allows for outputs on a per sample basis while avoiding the small differentials of successive sample differential calculations.

In accordance with another aspect of the present invention, differential values are determined using more than two samples. The associated process involves: receiving a series of data samples for a single-centered wavelength corresponding to a measurement; accessing first, second and third data samples of the series of data samples; using the first, second and third data samples to calculate a differential value; and using the differential value in determining the parameter value related to blood oxygen saturation. Preferably, multiple values, obtained over a portion of the pulsatile signal waveform are used to calculate a differential value. The optimal number of points depends in part on the sampling rate of the oximetry application. In a preferred implementation, samples are taken over a window of about 0.1 to 0.5 seconds, and, more preferably, about 0.25 to 0.33 seconds. For a sampling rate of 30 samples per second, this corresponds to about 3 to 15 and more preferably, about 7–10 samples per window. The use of multiple samples in this manner to determine a differential value allows for improved statistical analysis to reduce the effect of noise.

In a preferred implementation, a best-fit function analysis such as a linear regression analysis is performed on the multiple data points to compute a differential value. In this regard, a large number of points can be used to maximize noise rejection. It has been found, however, that such a best-fit function analysis, in addition to smoothing out noise effects, can undesirably smooth out abrupt signal changes corresponding to useful physiological information. Thus, in accordance with a further aspect of the present invention, certain points in the window of data points under analysis are emphasized in processing so that the best-fit function analysis can use a large number of points to maximize noise rejection while minimizing the reduction in differential amplitude (smoothing) associated with abrupt signal changes, e.g., due to high heart rates. In this regard, the best-fit function analysis may be conducted relative to a moving window of data points centered about a nominal instantaneous time interval for which the differential is to be calculated. Weighting selected center data points more heavily in the best-fit function analysis allows for noise reduction while reducing undesired smoothing. Such weighting may be accomplished by applying a suitable finite impulse response (FIR) filter window function to the windowed data. Examples include box, triangle, Gaussian and Blackman filter windows.

It will be appreciated that such processing yields a data set with reduced noise effects. This processed data set allows for increased accuracy in the blood oxygen saturation calculations. However, it has also been found advantageous to analyze the preprocessed, measured absorption data in order to identify noise levels associated with a particular data sets. For example, the preprocessed measured absorption data may be analyzed to identify a noise level associated with patient motion. Such a noise level may be used to exclude particular data sets from blood oxygen saturation calculations and/or to de-emphasize or otherwise compensate for motion effects. It will be appreciated that access to preprocessed measured absorption data may be preferred for such noise analyses.

In accordance with yet another aspect of the present invention, both preprocessed and postprocessed data are used in making a blood oxygen saturation determination. The associated method includes the steps of: storing a first set of preprocessed data based on a measured absorption signal; processing the first set of data to remove artifact therefrom and generate a second set of postprocessed data; accessing the first set of preprocessed data to calculate a first value for use in a blood oxygen saturation determination; accessing the second set of postprocessed data to determine a second value for use in a blood oxygen saturation determination; and using the first value and the second value to calculate a parameter value related to blood oxygen saturation. The process for removing artifact from the preprocessed data set may involve a differential value calculation as described above for rejecting noise. In such a case, the first value may be a differential value such as an NDA. The second value may be, for example, a noise threshold value for use in rejecting certain sample sets or an empirically derived correction factor to correct for motion artifact.

BRIEF DESCRIPTION OF THE DRAWINGS

For a more complete understanding of the present invention and further advantages thereof, reference is now made to the following Detailed Description taken in conjunction with the drawings, in which.

DETAILED DESCRIPTION

In the following description, the invention is set forth in the context of a two channel pulse oximetry system with motion correction. This embodiment is useful for illustrating the various aspects of the invention. However, it will be appreciated that certain aspects of the invention are useful in other contexts and in connection with other pulse oximetry implementations.

Figure 1:
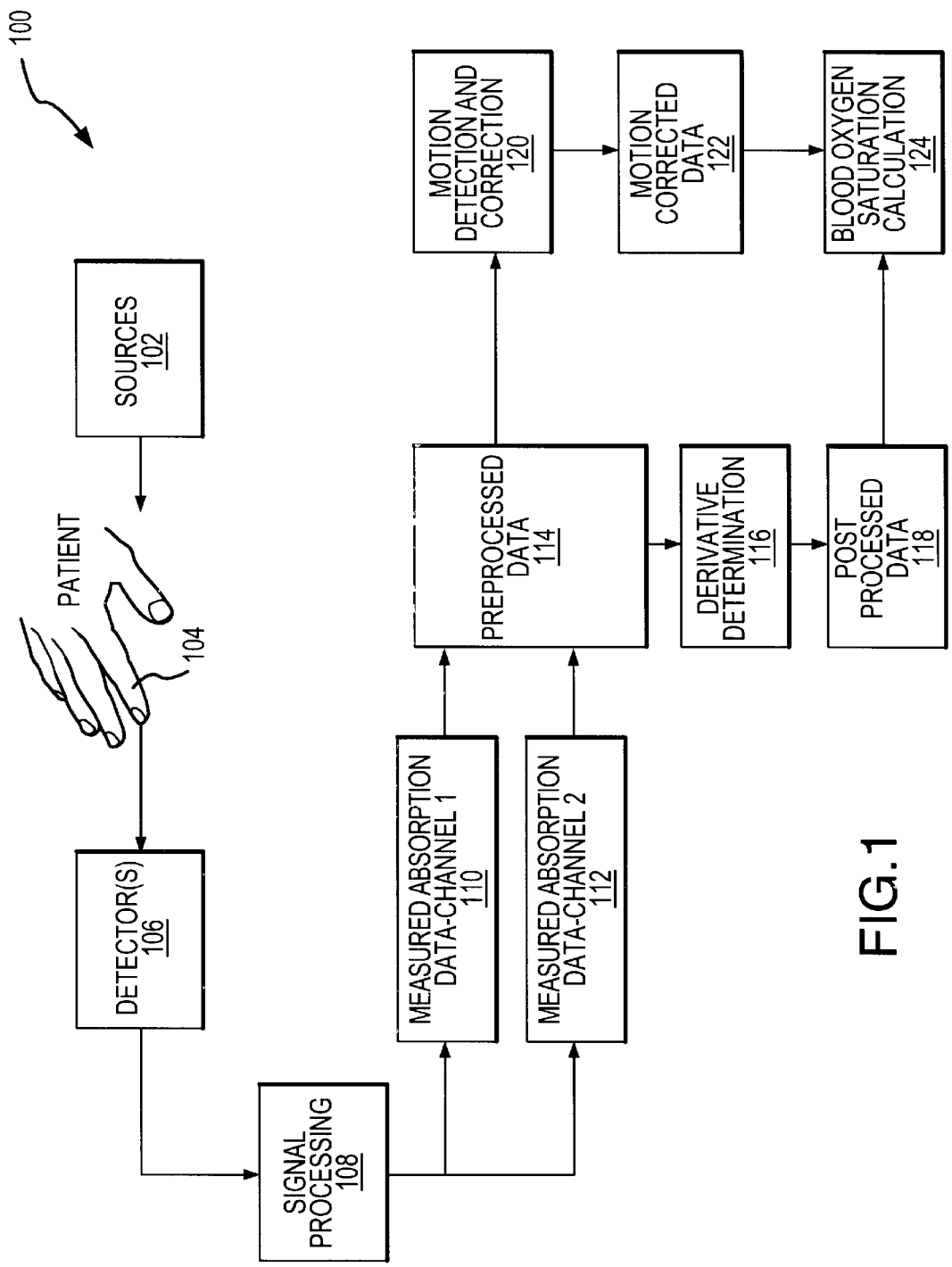
FIG. 1 is a schematic diagram of a pulse oximetry system in accordance with the present invention.

Referring to FIG. 1, a pulse oximetery system in accordance with the present invention is generally identified by the reference 100. Pulse oximetery systems generally include two or more light sources for transmitting light signals to an appendage of a patient. Light transmitted through or reflected from the patient's appendage is detected and blood oxygen saturation is determined based on absorption or attenuation of the signals. In the illustrated embodiment, the system 100 includes sources 102 which may be, for example, a red and an infrared transmitter. More than two sources operating at more than two wavelengths may be utilized, for example, for multi-component analysis. The signals from the sources 102 are transmitted to an appendage of the patient 104, in this case, a patient's finger and impinge on one or more detector(s) 106. The detector(s) 106 receive the optical signals and output an electrical detector signal representative of the received optical signals.

The detector signal is then processed by signal processing components 108. The signal processing components 108 may include various functional elements which may be embodied in hardware and/or software. For example, the signal processing components 108 may include an amplifier, an analog-to-digital converter, a de-multiplexer and other components for conditioning the signal. Such an amplifier may be utilized for various functions including converting the current signal from the detector into a voltage signal and filtering certain noise components. An analog-to-digital converter may be used to convert the received voltage signal into a series of digital values for processing by a digital processing unit. The de-multiplexer separates the detector signal into color channels e.g., red and infrared.

Accordingly, the signal processing components 108 in the illustrated embodiment provide two channels of measured absorption data 110 and 112. This data is stored in a preprocessed data buffer 114. The information stored in preprocessed data buffer 114 is used by a derivative determination module 116 to calculate derivatives as will be described in greater detail below. The resulting derivative values are stored in a postprocessed data buffer 118.

The preprocessed data is also used by a motion detection correction module 120. As noted above, motion of the patient 104 may result in path length changes of the transmitted signals that can result in errors in the blood oxygenation calculations if not addressed by the processing unit. In order to accurately identify and address such motion affected data, it is useful to analyze the data stored in preprocessed data buffer 114. In the illustrated embodiment, the motion detection and correction unit 120 accesses data from the preprocessed data buffer 114, and compensates for motion effects for improved accuracy. Specifically, the module 120 is operative to determine motion values associated with particular sets of data and to eliminate or adjust motion affected data sets as described in the co-pending U.S. patent application entitled "Pulse Oximetry Method and System with Improved Motion Connection" filed concurrently herewith and incorporated herein by reference. The resulting corrected data is stored in motion corrected data buffer 122. Data from each of the postprocessed data buffer 118 and the motion corrected data buffer 122 is then used by the blood oxygen saturation calculation module 124 to calculate a parameter related to blood oxygen saturation.

Figure 2:
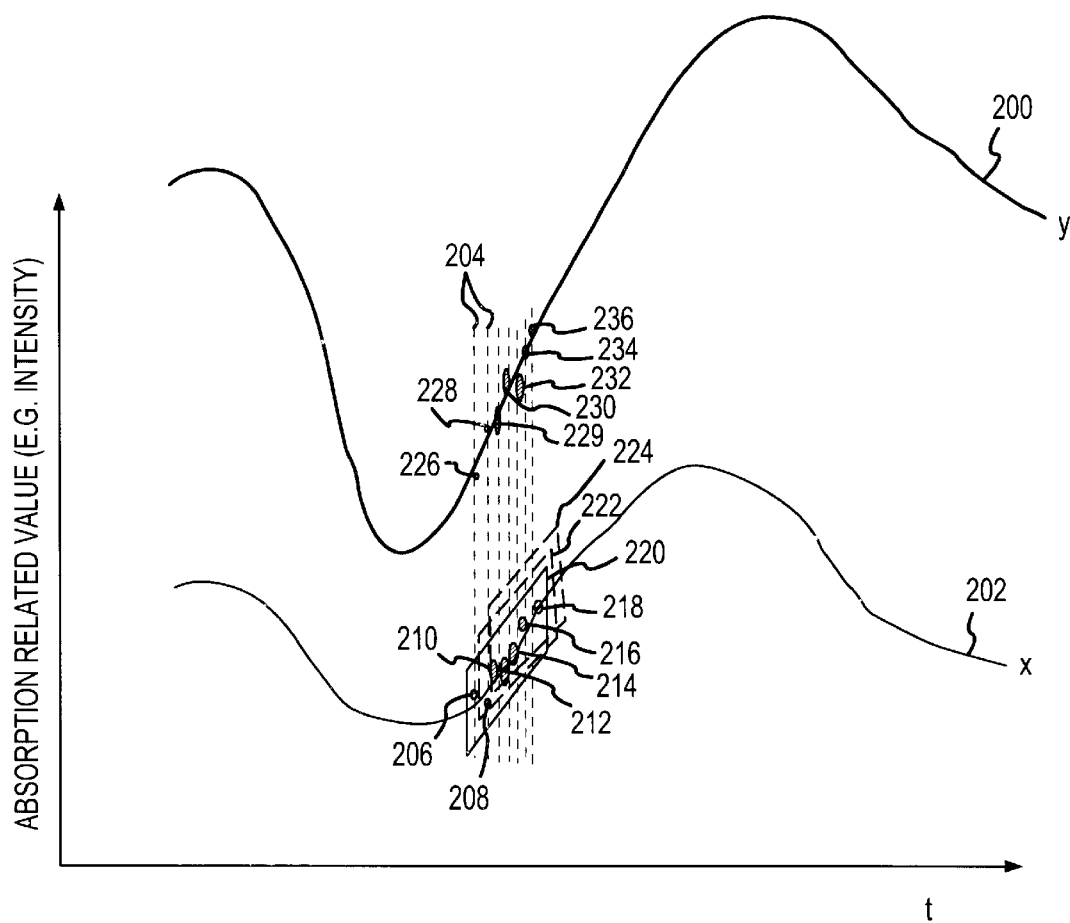
FIG. 2 is a graph illustrating a process for calculating differential values in accordance with the present invention.

FIG. 2 illustrates certain methodology for processing the measured absorption data. The measured absorption data generally includes a series of absorption related values (e.g. intensity) for a corresponding series of times for each of the two channels, in this case labeled channel X and channel Y. As discussed above, blood oxygen saturation is proportional to the ratio of the NdAs for the two channels. In FIG. 2, the signals 200 and 202 represent the pulsatile 'signal components of each of the channels. In reality, the measured absorption data for channel X includes a series of discrete absorption related values 206, 208, 210, 212, 214, 216 and 218 corresponding to particular times 204. Similarly, the measured absorption data for channel Y includes a discrete series of points 126, 128, 129, 130, 132, 134 and 136 associated with the same times 204.

In the illustrated implementation, NdAs for each of the channels are calculated using multiple data points. As shown, each of these data points is defined by a sample window 220, 222 and 224. Although the windows are only illustrated with respect to channel X, it will be appreciated that similar windows are employed to determine differential values for channel Y. In practice many data points may be included within each window. As will be understood upon consideration of the discussion below, samples across a given window are used to estimate a time derivative of attenuation or slope of the pulsatile signal for an instantaneous time interval corresponding to a center of the sampling window. This time derivative or slope is used in calculating an NdA. It will be appreciated that the window should therefore be small enough in relation to the expected pulsatile waveform so as to not unduly distort the calculated slope, but should be large enough to achieve the objective of reducing the impact of noise on the differential value calculation. In this regard, in a preferred implementation, a sampling rate of 30 samples per second is utilized and sampling window between about 0.1 to 0.5 seconds and, more preferably, between about 0.25 and 0.33 seconds is utilized. This corresponds to about 3 to 15 and, more preferably, about 7–10 samples per sampling window. For purposes of illustration, each of the illustrated windows 220, 222 and 224 are shown as including seven data points.

The data points within each window 220, 222 or 224 are used to establish a differential value nominally associated with the data sample about which the window is centered. Thus, the data points 206, 208, 210, 212, 214, 216 and 218 of window 220 are used to calculate a differential value such as an NdA for the center sample 212. As shown, a separate window is provided for each sample. Accordingly, even though multiple samples are utilized to calculate each differential value, a differential value is provided for each sample.

Various mathematical models can be used to calculate a differential value for a given sample based on the sample values within its window. In the illustrated implementation, the differential value is calculated based on a best-fit function analysis. Such a best-fit function analysis may involve, for example, a linear or non-linear regression analysis. A linear regression analysis allows for simplified processing and will be described in detail below.

In its simplest form, each of the samples within a window may be given equal weight in the linear regression analysis so as to determine the line which best fits all of the data points. The slope of this line thus provides a basic differential value for the center point of the window. However, certain processing advantages are achieved by converting this basic differential value into an NdA. This can be accomplished by calculating the NdA as the quotient of the slope of the best-fit line divided by an average of the DC components of the samples within the window, e.g., the sum of the DC components of samples 206, 208, 210, 212, 214, 216 and 218 divided by seven.

It has been found, however, that such an unweighted linear regression analysis not only smoothes out noise effects but can also smooth out abrupt signal changes corresponding to useful physiological information, for example, in the case of a patient with a rapid heart rate and therefore steep signal slopes. Accordingly, a preferred linear regression analysis involves weighting certain center points within the window more heavily than points closer to the window edges. This is illustrated graphically in FIG. 2 where the center samples 210, 212 and 214 are illustrated as being larger than the peripheral data points 206, 208, 216 and 218.

Figure 4:
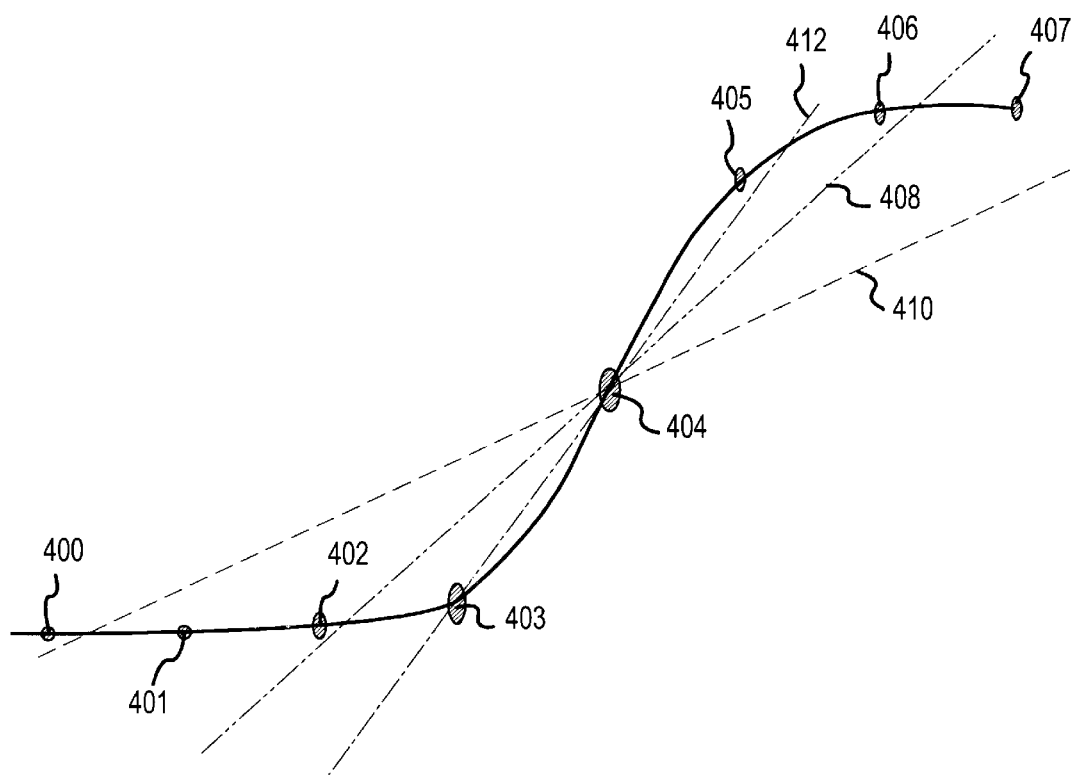
FIG. 4 is a graph illustrating the effect of weighting on the determined differential value in accordance with and in accordance with the present invention.

This effect is further illustrated in FIG. 4. Specifically, FIG. 4 shows a number of data points 400–407 of a given sampling window. Line 408 reflects the slope that would be calculated as the numerator of an NdA if only the two successive center data points 403 and 404 were used for the differential value calculation. Such a calculation is highly sensitive to noise as discussed above. Best-fit line 410 illustrates the results of an unweighted linear regression analysis. Such an analysis typically derives the line 410 by a least square errors analysis wherein each data sample is given equal weight. That is, the linear regression algorithm attempts to minimize the value of the sum of the series of error terms for the data points 400–407 where each error term is the square of the deviation of the subject data point from the putative best-fit line. However, as noted above, such an unweighted window analysis is substantially affected by data points at the edges of the window, and may smooth out abrupt signal changes reflecting meaningful physiological data.

It has been found that improved results can be achieved by weighting the data points near the center of the window relative to those near the window edges. It will be appreciated that the degree of weighting, e.g., the number of sample points weighted and the weighting factor applied to the weighted and/or "unweighted" sample points, can be selected so as to balance noise elimination against undesired smoothing. That is, the greater the weighting the more accurately the calculated differential values will track abrupt slope changes. However, greater weighting also reduces noise elimination. On the other hand, a lesser degree of weighting optimizes noise elimination but at the cost of allowing some degree of unwanted smoothing.

FIGS. 5a–5d show various models for weighting data points in the center of a sampling window relative to points at the window edges. The figures show such weighting graphically by plotting a weighting factor against point number, where points 1 and 8 represent the window edges and points 4 and 5 are at the center of the sampling window. The weighting factors can be applied as coefficients in the algorithm to determine the NdA. Specifically, an NdA can be calculated as a quotient where the numerator is the slope of a best-fit line drawn relative to the data points of a window and the denominator is an average value for the DC detector signal component.

As noted above, in an unweighted linear regression analysis, the best-fit line is defined by minimizing the sum of the error squared terms over a window. Weighting can be accomplished by applying a weighting coefficient to one or more (up to all) of the error squared terms used to define the best-fit line. By applying a larger weighting coefficient to the terms representing the middle of the window, any deviation between the putative best-fit line and these data points is amplified and thus factors heavily in the analysis. By contrast, deviations relating to points located nearer to the window edges are relatively diminished in the analysis. The weighting coefficients are also applied directly to the DC value for each data point in determining an average dc value for the denominator of the NdA.

As a result, as shown in FIG. 4, the slope of the line 408 determined by a weighted linear regression analysis may more closely match the slope of a line 412 drawn through the two center points 403 and 404, than would the slope of a line 410 determined using an unweighted linear regression analysis. Thus, the weighting achieves the desired effect of reducing the sensitivity to noise while not unduly smoothing out signal components corresponding to useful physiological information.

Figure 5A:
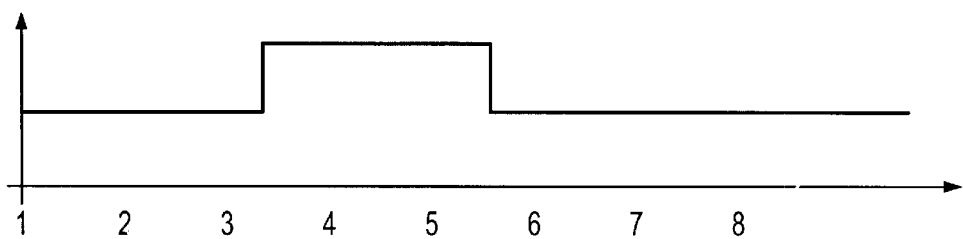
FIGS. 5a–5d illustrate various weighting models in accordance with the present invention.
Figure 5B:
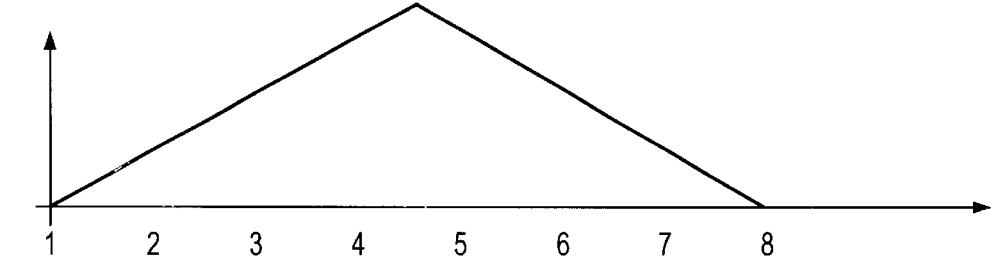
Figure 5C:
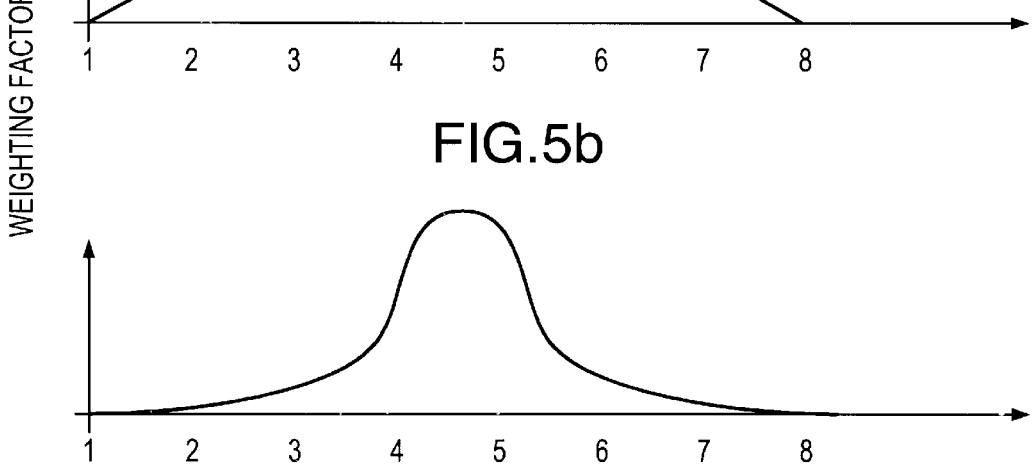
Figure 5D:
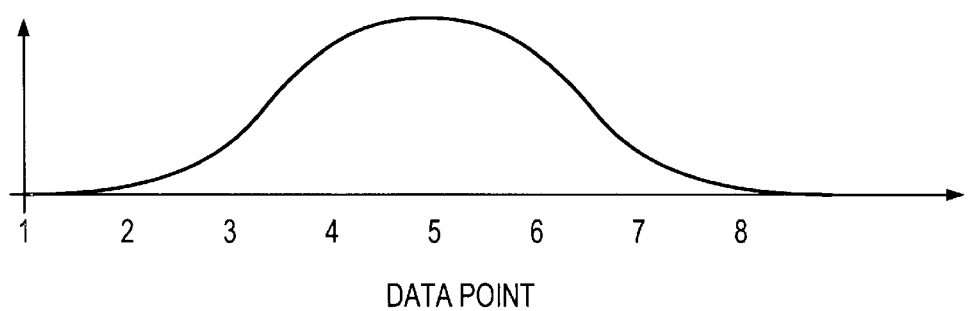

Referring to the weighting models of FIGS. 5a–5d, FIG. 5a illustrates a box window where points 1, 2, 3 and 6, 7, 8 are weighted by a first factor and the center points 4 and 5 are weighted by a second, greater factor. FIG. 5b illustrates a triangle window where points 1 and 8 are weighted by a factor of zero and, in between, the weighting factors increase, with the maximum weighting factor applied to the center points 4 and 5. FIG. 5c illustrates a Gaussian distribution of the weighting factor over the window, and 5d shows a sinusoidal of, more accurately, cosinusoidal distribution. It will be appreciated that many other weighting models are possible.

In a preferred implementation, the function of a low pass FIR filter window is utilized to achieve a weighting effect. Any low pass FIR filter window that does not apply negative weighting factors behaves well under the regression analysis. Examples are box, triangle, Gaussian, and Blackman filter windows, where the Blackman window has proved especially effective. Thus, although the functions of standard linear filters are used as weights, the resulting weighting algorithms are not linear. The weighting does not produce the same results as pre-filtering or post-filtering the window. The weighting produces the desired effect of producing a differential value of substantially full magnitude (little or no smoothing) while allowing a larger number of points in the regression analysis.

The following pseudo code implements a preferred NdA calculation.

```
Function [nda]=normdal (indata)
% [nda]=normda (indata)
winsz=9;

x=linspace (-winsz/2,winsz/2,winsz);
window=Blackman (winsz)';
window=window/sum (window); % nomalize Sy=conv (indata,window);
Sx=0; % Sx=sum (x.*window);
Sxx=sum (x.*x.*window);
Sxy=conv (indata ,x.*window);

Slope=Sxy/Sxx; % slope=(Sxy-Sx.*Sy)./(Sxx-Sx.*Sx);
avr=Sy;
nda=slope ./avr;
nda=nda (winsz:size(nda,2)-winsz);
```

By centering the window about "zero" time, the Sx term drops out. The Sx^2 term, Sxx is a constant, as are the terms in the convolution with the vector x* window. The net result is code that has a few multiply/accumulates per window. As Sxx is a constant for both channels, the division by this term can be left out or done by multiplying by a 1/Sxx constant. Also, the average term (the average DC value used for normalization) is weighted by the same weighting by the regression terms in order to achieve the desired normalization effect.

Figure 3:
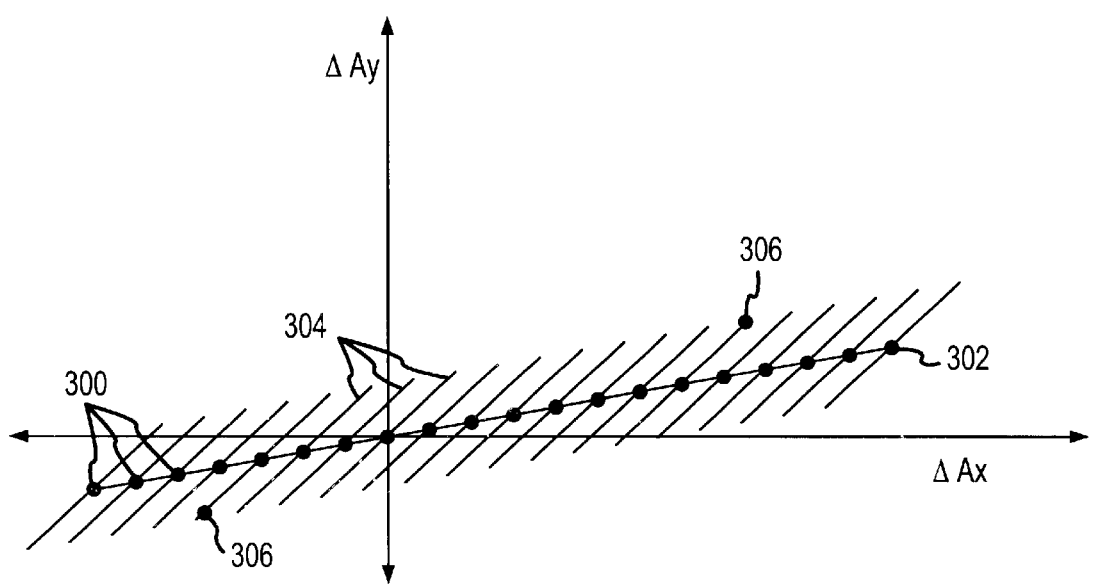
FIG. 3 is a graph illustrating a process for calculating an oxygen saturation value based on differential absorption ratios; in accordance with the present invention.

FIG. 3 illustrates the process for calculating blood oxygen saturation based on the NdAs of the X and Y channels. In FIG. 3, the NdAs for the X and Y channels are designated by $\Delta A_x$ and $\Delta A_y$. Specifically, for each sample, the value of the NdA for the X channel is plotted against the value of the NdA for the Y channel to define a number of data points 300. The data points 300 define line 302. Mathematically, this line may be determined by using a best-fit function analysis such as a linear regression analysis on the data points 300. The slope of the line 302 is directly proportional to the blood oxygen saturation. It should be appreciated that the illustrated points are idealized in that they are precisely colinear. In reality, patient motion and other effects will typically cause the points 300 to be somewhat dispersed. In particular, motion will tend to cause an offset of the affected points 306 along a typically 45 degree offset line 304 as illustrated. This phenomena is utilized to identify motion affected data and to compensate for such effects as set forth in the above-noted patent application filed concurrently herewith and incorporated herein by reference. Thus, the blood oxygen saturation calculation involves determining derivative information as described above using pre-processed data. In the illustrated embodiment, motion affected data points 306 may be eliminated or de-weighted prior to performing the best-fit function analysis, e.g. linear regression analysis to determine the slope of the line 302.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method for use in determining a parameter value related to blood oxygenation in a pulse oximeter that provides a detector output including a series of values related to light absorption by a tissue under consideration for each of first and second centered wavelengths, the method comprising the steps of:

obtaining a first instantaneous differential value related to a first instantaneous time interval by defining a sampling window having a time dimension greater than said instantaneous time interval, said first instantaneous differential value being calculated by using at least three separate values, within said window, of said series of values related to light absorption by said tissue under consideration for said first centered wavelength, and applying different effective weights to different ones of said values within said window; and using said first instantaneous differential value in connection with calculating said parameter value related to blood oxygenation.

2. A method as set forth in claim 1, wherein said sampling window includes said at least three separate values at said first instantaneous time interval and said sampling window has a time dimension of between about 0.1 to 0.5 seconds.

3. A method as set forth in claim 2, wherein said window has a time dimension of between about 0.25 and 0.33 seconds.

4. A method as set forth in claim 1, wherein, at said first instantaneous time interval, said sampling window includes between about 3–15 values of said series of values.

5. A method as set forth in claim 1, wherein, at said first instantaneous time interval, said sampling window includes between about 7–10 values of said series of values.

6. A method as set forth in claim 1, wherein said first instantaneous differential value is calculated by performing a best-fit function analysis relative to said at least three separate values of said series of values.

7. A method as set forth in claim 6, wherein said best-fit function analysis is a linear regression analysis.

8. A method as set forth in claim 1, wherein said effective weights are related to locations of said different ones of said values relative to said window.

9. A method as set forth in claim 1, wherein said effective weights are applied by employing a finite impulse response (FIR) filter window function to the values within the said window.

10. A method as set forth in claim 9, wherein said FIR function includes one of a box, triangle, Guassian and Blackman window function.

11. A method as set forth in claim 1, further comprising the steps of:

obtaining a second instantaneous differential value related to said first instantaneous time interval, said second instantaneous differential value being calculated using at least three separate values of said series of values related to light absorption by said tissue under consideration for said second centered wavelength; and relating said first and second instantaneous differential values to get a data point related to said parameter values.

12. A method as set forth in claim 11, further comprising the steps of:

repeating said steps of 1) obtaining said first instantaneous differential value and 2) obtaining said second instantaneous differential value, for a number of additional instantaneous time intervals within a sampling period;

for said first instantaneous time interval and each of said additional instantaneous time intervals, using said first and second instantaneous differential values to obtain a data point related to said parameter value, thereby generating a set of data points for said sampling period; and using said set of data points to obtain said parameter value.

13. A method as set forth in claim 12, wherein said step of using said set of data points comprises performing a best-fit function analysis relative to said data points.

14. A method for use in determining a parameter related to blood oxygenation in a pulse oximetry system, the oximetry system providing first detector signal information indicative of light absorption at a first wavelength over a time period by a tissue-under-test and second detector signal information indicative of light absorption at a second wavelength over the time period by the tissue-under-test, each of the first and second detector sign al information including a series of absorption related values for a corresponding series of times within said time period, said method comprising the steps of:

first determining, for each of the first and second detector signal information, a first differential value using more than one of said absorption related values;

second determining, for each of the first and second detector signal information, a second differential value using more than one of said absorption related values, wherein at least one of said absorption related values used to determine said second differential value is different than any of said absorption related values used to determine said first differential value; said steps of first and second determining thereby yielding first and second differential values for each of said first and second detector signal information; and third determining, using said first and second differential values for each of said first and second detector signal information, a parameter value of said parameter related to blood oxygenation;

wherein, in said steps of first and second determining, each of said first and second differential values is calculated using a first absorption related value of said series of absorption related values for a first time within said time period and a second absorption related value of said series of absorption related values for a second time within said time period, said first and second absorption related values being separated by an intervening absorption related value for an intervening time between said first and second times; and wherein each of said steps of first and second determining comprises defining a sampling window having a time dimension less than said time period and encompassing said first and second times and said steps of first and second determining involve applying different effective weights to different ones of said values within said window.

15. A method as set forth in claim 14, wherein said sampling window has a time dimension of between about 0.1 to 0.5 seconds.

16. A method as set forth in claim 15, wherein said window has a time dimension of between about 0.25 and 0.33 seconds.

17. A method as set forth in claim 14, wherein said sampling window includes between about 3–15 values of said series of values.

18. A method as set forth in claim 14, wherein said sampling window includes between about 7–10 values of said series of values.

19. A method as set forth in claim 14, wherein each of said first and second differential values is calculated by performing a best-fit function analysis relative to said first and second absorption related values.

20. A method as set forth in claim 19, wherein said best-fit function analysis is a linear regression analysis.

21. A method as set forth in claim 14, wherein said effective weights are related to locations of said different ones of said values relative to said window.

22. A method as set forth in claim 14, wherein said effective weights are applied by employing a finite impulse response (FIR) filter window function to the values within the said window.

23. A method as set forth in claim 22, wherein said FIR function includes one of a box, triangle, Guassian and Blackman window function.

24. A pulse oximeter, comprising:

a source system for transmitting light signals relative to tissue under consideration, said light signals including a first signal having a first centered wavelength and a second signal having a second centered wavelength;

a detector system for receiving said light signals transmitted relative to said tissue under consideration and providing a series of values related to light attenuation by said tissue under consideration for each of first and second centered wavelengths; and a processor operative for:
obtaining a first instantaneous differential value related to a first instantaneous time interval, said first instantaneous differential value being calculated using at least three separate values of said series of values related to light absorption by said tissue under consideration for said first centered wavelength; and using said first instantaneous differential value in connection with calculating said parameter value related to blood oxygenation; and defining a sampling window having a time dimension greater than said instantaneous time interval; and wherein said step of obtaining said first instantaneous differential value involves applying different effective weights to different ones of said values within said window.

25. A pulse oximeter as set forth in claim 24, wherein said source system is operative for transmitting time division multiplexed signals.

26. A pulse oximeter as set forth in claim 24, wherein said source system is operative for transmitting frequency division multiplexed signals.

27. A pulse oximeter as set forth in claim 24, wherein said sampling window includes said at least three separate values at said first instantaneous time interval and said sampling window has a time dimension of between about 0.1 to 0.5 seconds.

28. A pulse oximeter as set forth in claim 27, wherein said window has a time dimension of between about 0.25 and 0.33 seconds.

29. A pulse oximeter as set forth in claim 24, wherein, at said first instantaneous time interval, said sampling window includes between about 3–15 values of said series of values.

30. A pulse oximeter as set forth in claim 24, wherein, at said first instantaneous time interval, said sampling window includes between about 7–10 values of said series of values.

31. A pulse oximeter as set forth in claim 24, wherein said first instantaneous differential value is calculated by performing a best-fit function analysis relative to said at least three separate values of said series of values.

32. A pulse oximeter as set forth in claim 31, wherein said best-fit function analysis is a linear regression analysis.

33. A pulse oximeter as set forth in claim 24, wherein said effective weights are related to locations of said different ones of said values relative to said window.

34. A pulse oximeter as set forth in claim 24, wherein said effective weights are applied by employing a finite impulse response (FIR) filter window function to the values within the said window.

35. A method as set forth in claim 34, wherein said FIR function includes one of a box, triangle, Guassian and Blackman window function.

36. A pulse oximeter as set forth in claim 24, wherein said processor is further operative for:

obtaining a second instantaneous differential value related to said first instantaneous time interval, said second instantaneous differential value being calculated using at least three separate values of said series of values related to light absorption by said tissue under consideration for said second centered wavelength; and relating said first and second instantaneous differential values to get a data point related to said parameter values.

37. A pulse oximeter as set forth in claim 36, wherein said processor is further operative for:

repeating said steps of 1) obtaining said first instantaneous differential value and 2) obtaining said second instantaneous differential value, for a number of additional instantaneous time intervals within a sampling period;

for said first instantaneous time interval and each of said additional instantaneous time intervals, using said first and second instantaneous differential values to obtain a data point related to said parameter value, thereby generating a set of data points for said sampling period; and using said set of data points to obtain said parameter value.

38. A pulse oximeter as set forth in claim 37, wherein said processor uses said set of data points by performing a best-fit function analysis relative to said data points.

* * * * *